US010290378B1

(12) United States Patent
Bujko

(10) Patent No.: US 10,290,378 B1
(45) Date of Patent: May 14, 2019

(54) WEARABLE DEVICE TO ALERT AUTHORITIES WHEN A WEARER IS EXPERIENCING AN EPISODE RELATED TO A MENTAL ILLNESS

(71) Applicant: Tanya Lee Bujko, Rathdrum, ID (US)

(72) Inventor: Tanya Lee Bujko, Rathdrum, ID (US)

(*) Notice: Subject to any disclaimer, the term of this patent is extended or adjusted under 35 U.S.C. 154(b) by 0 days.

(21) Appl. No.: 15/984,836

(22) Filed: May 21, 2018

(51) Int. Cl.
*G06F 19/00* (2018.01)
*G16H 50/50* (2018.01)
*G08B 25/01* (2006.01)
*G01C 21/20* (2006.01)

(52) U.S. Cl.
CPC ............. *G16H 50/50* (2018.01); *G01C 21/20* (2013.01); *G08B 25/016* (2013.01)

(58) Field of Classification Search
CPC .................................................. G16H 50/50
USPC .............. 340/539.12, 573.1, 573.4, 286.07
See application file for complete search history.

(56) References Cited

U.S. PATENT DOCUMENTS

| | | | | |
|---|---|---|---|---|
| 2009/0121863 A1* | 5/2009 | Prior | ....................... | G08B 21/04 340/539.12 |
| 2011/0118555 A1* | 5/2011 | Dhumne | ................... | A61B 5/16 600/300 |
| 2015/0370994 A1* | 12/2015 | Madan | ................. | G06F 19/3418 705/3 |
| 2017/0116845 A1* | 4/2017 | See | ....................... | G08B 25/016 |

* cited by examiner

*Primary Examiner* — Brent Swarthout
(74) *Attorney, Agent, or Firm* — The Iwashko Law Firm, PLLC; Lev Ivan Gabriel Iwashko

(57) ABSTRACT

A wearable device to communicate with a receiver, the wearable device including a wearable portion to contact a skin of a user when the wearable device is worn by the user, and a transmitter including a button and circuitry to transmit a signal to the receiver in response to the button being depressed, such that the signal received by the receiver indicates that a psychotic episode of a person with a mental illness is taking place at a location near the wearable device.

4 Claims, 2 Drawing Sheets

WEARABLE DEVICE TO ALERT AUTHORITIES WHEN A WEARER IS EXPERIENCING AN EPISODE RELATED TO A MENTAL ILLNESS

BACKGROUND

1. Field

The present general inventive concept relates generally to a wearable device to alert authorities when a wearer is experiencing an episode related to a mental illness.

2. Description of the Related Art

According to the National Alliance on Mental Illness, one in five Americans experience some type of mental illness, and nearly one in twenty-five adult Americans live with a serious mental illness, approximately 10 million adults. On occasions where a serious situation calls for police intervention, it becomes clear that the police do not know how to handle crisis situations, where an individual who may have the appearance of being a threat may simply have a mental illness, often escalating into using deadly force.

Therefore, there is a need for a system that provides persons with mental illness and their caregivers with a device that alerts authorities or mental health professionals in the case of a life-threatening issue.

There is also a need for a device that helps reduce the risk of violence against mentally ill people when they're in the midst of a potential episode or breakdown, or otherwise.

SUMMARY

The present general inventive concept provides a wearable device to alert authorities when a wearer is experiencing an episode related to a mental illness.

Additional features and utilities of the present general inventive concept will be set forth in part in the description which follows and, in part, will be obvious from the description, or may be learned by practice of the general inventive concept.

The foregoing and/or other features and utilities of the present general inventive concept may be achieved by providing a wearable device to communicate with a receiver, the wearable device including a wearable portion to contact a skin of a user when the wearable device is worn by the user, and a transmitter including a button and circuitry to transmit a signal to the receiver in response to the button being depressed, such that the signal received by the receiver indicates that a psychotic episode of a person with a mental illness is taking place at a location near the wearable device.

The wearable device may include at least one of metal, plastic, and a precious stone.

The signal may allow the receiver to track the wearable device via GPS.

The wearable device may be at least one of a bracelet and a necklace.

BRIEF DESCRIPTION OF THE DRAWINGS

These and/or other features and utilities of the present generally inventive concept will become apparent and more readily appreciated from the following description of the embodiments, taken in conjunction with the accompanying drawings of which.

DETAILED DESCRIPTION

Various example embodiments (a.k.a., exemplary embodiments) will now be described more fully with reference to the accompanying drawings in which some example embodiments are illustrated. In the figures, the thicknesses of lines, layers and/or regions may be exaggerated for clarity.

Accordingly, while example embodiments are capable of various modifications and alternative forms, embodiments thereof are shown by way of example in the figures and will herein be described in detail. It should be understood, however, that there is no intent to limit example embodiments to the particular forms disclosed, but on the contrary, example embodiments are to cover all modifications, equivalents, and alternatives falling within the scope of the disclosure. Like numbers refer to like/similar elements throughout the detailed description.

It is understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art. However, should the present disclosure give a specific meaning to a term deviating from a meaning commonly understood by one of ordinary skill, this meaning is to be taken into account in the specific context this definition is given herein.

Figure 1:
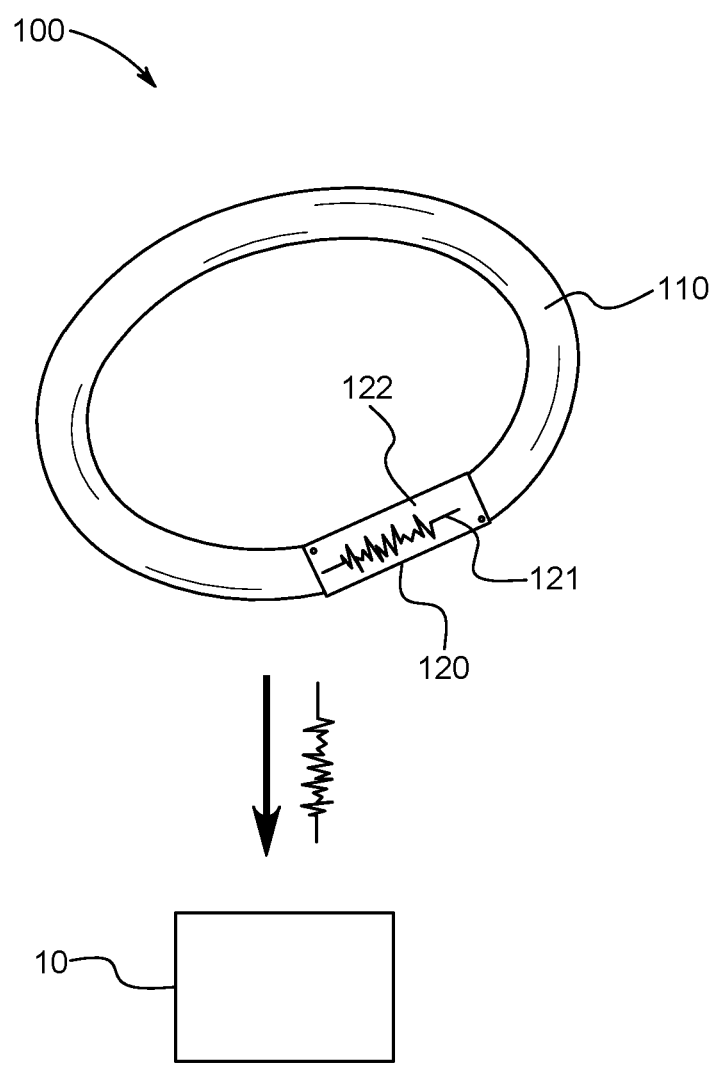
FIG. 1 illustrates a wearable device for a caregiver to alert authorities when an individual is experiencing an episode related to a mental illness, according to an exemplary embodiment of the present general inventive concept.

FIG. 1 illustrates a wearable device 100 for a caregiver to alert authorities when an individual is experiencing an episode related to a mental illness, according to an exemplary embodiment of the present general inventive concept.

The wearable device 100 may be shaped like a bracelet that may be worn by a user, and may be made from plastic, metal (e.g., gold, silver, platinum, bronze, etc.), cloth, precious stones, rope, wiring, etc., but is not limited thereto.

The wearable device 100 may include a wearing portion 110, and a transmitter 120.

The wearing portion 110 may be designed like a bracelet to contact skin of a user when worn by the user.

The transmitter 120 may include a button 121 that may be pressed by a caregiver of a person with a mental illness when the person with the mental illness is experiencing a psychotic episode.

The transmitter 120 may include circuitry 122 therein to transmit a silent signal from the wearable device 100 to hospitals, first response teams, police, and mental health professionals. In other words, the transmitter 120 may transmit the silent signal from the wearable device 100 to a receiver 10 at the hospitals or police stations.

The receiver 10 may have a display, emit a noise, or have any other indicator to alert authorities of a location of the wearable device 100 when the button 121 has been depressed. As such, the receiver 10 may also have GPS tracking capabilities to help locate the wearable device 100. Also, the signal received by the receiver 10 may indicate via display or sound that a psychotic episode of a person with a mental illness is taking place at a location near the wearable device 100.

More specifically, the wearable device 100 is intended to be worn by a person who is a caregiver of an individual with a mental illness. If the individual with the mental illness experiences a violent psychotic episode, the caregiver may depress the button 121 so that the transmitter 120 sends the silent signal to the receiver 10 at hospitals, first response teams, police, and mental health professionals, so that the individual with the mental illness is not treated like a criminal, but instead, like a person with a sickness. As such, violence and abuse may be avoided, because the police will already understand that the individual causing a disturbance has a mental illness.

Figure 2:
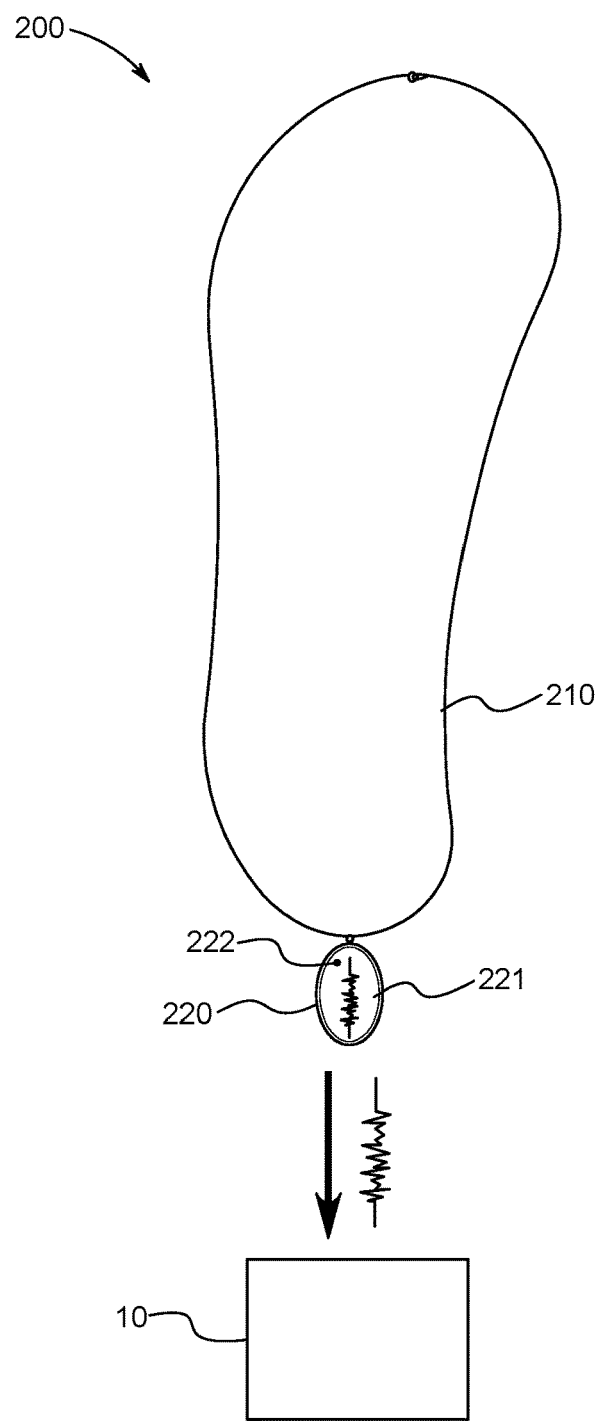
FIG. 2 illustrates a wearable device for a caregiver to alert authorities when an individual is experiencing an episode related to a mental illness, according to another exemplary embodiment of the present general inventive concept.

FIG. 2 illustrates a wearable device 200 for a caregiver to alert authorities when an individual is experiencing an episode related to a mental illness, according to another exemplary embodiment of the present general inventive concept.

The wearable device 200 may be shaped like a necklace that may be worn by a user, and may be made from plastic, metal (e.g., gold, silver, platinum, bronze, etc.), cloth, precious stones, rope, wiring, etc., but is not limited thereto.

The wearable device 200 may include a wearing portion 210, and a transmitter 220.

The wearing portion 210 may be designed like a necklace to contact skin of a user when worn by the user.

The transmitter 220 may include a button 221 that may be pressed by a caregiver of a person with a mental illness when the person with the mental illness is experiencing a psychotic episode.

The transmitter 220 may include circuitry 222 therein to transmit a silent signal from the wearable device 200 to hospitals, first response teams, police, and mental health professionals. In other words, the transmitter 220 may transmit the silent signal from the wearable device 200 to a receiver 10 at the hospitals or police stations.

The receiver 10 may have a display, emit a noise, or have any other indicator to alert authorities of a location of the wearable device 200 when the button 221 has been depressed. As such, the receiver 10 may also have GPS tracking capabilities to help locate the wearable device 200. Also, the signal received by the receiver 10 may indicate via display or sound that a psychotic episode of a person with a mental illness is taking place at a location near the wearable device 200.

More specifically, the wearable device 200 is intended to be worn by a person who is a caregiver of an individual with a mental illness. If the individual with the mental illness experiences a violent psychotic episode, the caregiver may depress the button 221 so that the transmitter 220 sends the silent signal to the receiver 10 at hospitals, first response teams, police, and mental health professionals, so that the individual with the mental illness is not treated like a criminal, but instead, like a person with a sickness. As such, violence and abuse may be avoided, because the police will already understand that the individual causing a disturbance has a mental illness.

Although a few embodiments of the present general inventive concept have been shown and described, it will be appreciated by those skilled in the art that changes may be made in these embodiments without departing from the principles and spirit of the general inventive concept, the scope of which is defined in the appended claims and their equivalents.

The invention claimed is:

1. A wearable device wearable by a caregiver of a person with a mental illness, the wearable device designed to communicate with a receiver, the wearable device comprising:
   a wearable portion to contact a skin of the caregiver when the wearable device is worn by the caregiver; and
   a transmitter including a button and circuitry to transmit a signal to the receiver in response to the button being depressed by the caregiver based on a determination by the caregiver that the person with the mental illness is experiencing a psychotic episode, such that the signal received by the receiver indicates that the psychotic episode of the person with the mental illness is taking place at a location near the wearable device, such that authorities in possession of the receiver are notified that the person with the mental illness is at the location near the wearable device, in order to prevent the authorities from exerting excessive force against the person with the mental illness.

2. The wearable device of claim 1, wherein the wearable device is comprised of at least one of metal, plastic, and a precious stone.

3. The wearable device of claim 1, wherein the signal allows the receiver to track the wearable device via GPS.

4. The wearable device of claim 1, wherein the wearable device is at least a portion of at least one of a bracelet and a necklace.

* * * * *